US011998566B1

(12) United States Patent
Abdallah et al.

(10) Patent No.: US 11,998,566 B1
(45) Date of Patent: Jun. 4, 2024

(54) **METHOD OF SYNTHESIZING A SILVER NANOPARTICLE COMPOSITION USING AN EXTRACT OF *Salsola tetrandra***

(71) Applicant: KING FAISAL UNIVERSITY, Al-Ahsa (SA)

(72) Inventors: Basem Mohamed Abdallah, Hofouf (SA); Enas Mohamed Ali Abd-Elkader, Hofouf (SA)

(73) Assignee: KING FAISAL UNIVERSITY, Al-Ahsa (SA)

(*) Notice: Subject to any disclaimer, the term of this patent is extended or adjusted under 35 U.S.C. 154(b) by 0 days.

(21) Appl. No.: 18/508,971

(22) Filed: Nov. 14, 2023

(51) Int. Cl.
*A61K 33/38* (2006.01)
*A61K 36/21* (2006.01)
*A61P 31/10* (2006.01)

(52) U.S. Cl.
CPC .............. *A61K 33/38* (2013.01); *A61K 36/21* (2013.01); *A61P 31/10* (2018.01)

(58) Field of Classification Search
CPC ........... B82Y 5/00; B82Y 30/00; B82Y 40/00; A61K 33/38; A61K 36/21; A61P 31/10
See application file for complete search history.

(56) References Cited

U.S. PATENT DOCUMENTS

2020/0129577 A1* 4/2020 Braguti .................. A61K 33/34

OTHER PUBLICATIONS

Dalia M. Rasheed, Soheir M. El Zalabani, Mahmoud A. Koheil, Hala M. El-Hefnawy & Mohamed A. Farag Metabolite profiling driven analysis of Salsola species and their anti-acetylcholinesterase potential, DOI: 10.1080/14786419.2013.832676.
Mai H. ElNaggar, Wagdy M. Eldehna, Mohammed A. S. Abourehab, & Fatma M. Abdel Bar, The old world salsola as a source of valuable secondary metabolites endowed with diverse pharmacological activities: a review DOI: 10.1080/14756366.2022.2102005.
Samar S. A. Murshid, Dana Atoum, Dina R. Abou-Hussein, Hossam M. Abdallah, Rawan H. Hareeri, Haifa Almukadi, RuAngelie Edrada-Ebel Genus Salsola: Chemistry, Biological Activities and Future Prospective—A Review, DOI: 10.3390/plants11060714.
Enas M Ali & Basem M Abdallah Effective Inhibition of Invasive Pulmonary Aspergillosis by Silver Nanoparticles Biosynthesized with Artemisia sieberi Leaf, DOI: 10.3390/nano12010051.
Widadh Klein, Enas Ismail, Ernest Maboza, Ahmed A. Hussein and Razia Z. Adam Green-Synthesized Silver Nanoparticles: Antifungal and Cytotoxic Potential for Further Dental Applications, DOI: 10.3390/jfb14070379.
M Habib Oueslati , Hichem Ben Jannet, Zine Mighri, J Chriaa, Pedro M Abreu Phytochemical constituents from Salsola tetrandra, DOI: 10.1021/np060222w.

(Continued)

*Primary Examiner* — Hong Yu
(74) *Attorney, Agent, or Firm* — Nath, Goldberg & Meyer; Richard C. Litman

(57) ABSTRACT

*Salsola tetrandra* silver nanoparticles (ST-AgNPs) can be prepared by providing a *Salsola tetrandra* extract and combining the *Salsola tetrandra* extract with silver nitrate. The mixture can be heated to complete the bio-reduction process and provide the *Salsola tetrandra* silver nanoparticle composition. The *Salsola tetrandra* silver nanoparticles can be used to treat or inhibit a fungal infection, such as invasive pulmonary aspergillosis.

16 Claims, 1 Drawing Sheet

(56) References Cited

OTHER PUBLICATIONS

Dongyang Wang, Baiji Xue, Lin Wang, Yidi Zhang, Lijun Liu & Yanmin Zhou Fungus-mediated green synthesis of nano-silver using Aspergillus sydowii and its antifungal/antiproliferative activities, DOI:10.1038/s41598-021-89854-5.

Abdelmageed M. Othman, Maysa A. Elsayed, Naser G. Al-Balakocy, Mohamed M. Hassan & Ali M. Elshafei Biosynthesis and characterization of silver nanoparticles induced by fungal proteins and its application in different biological activities DOI: 10.1186/s43141-019-0008-1.

\* cited by examiner

METHOD OF SYNTHESIZING A SILVER NANOPARTICLE COMPOSITION USING AN EXTRACT OF *Salsola tetrandra*

BACKGROUND

1. Field

The disclosure of the present patent application relates to silver nanoparticles, and particularly, to silver nanoparticles synthesized using chlorophyll derivatives.

2. Description of the Related Art

Recently, nanoparticles have demonstrated important uses in a variety of fields. Nanoparticles have been used in electronics, sensing, optics, and medicine, for example.

Synthesis of nanoparticles has been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce by-products that pose increased risks to human health and the environment.

In recent years, green or environmentally friendly chemical methods have been developed to prepare nanoparticles using plant extracts. Green chemistry has the advantage of being safer, faster, environmentally friendly, and economical. However, the rise of green methods of preparing nanoparticles has also demonstrated that the activities and characteristics of the nanoparticles vary significantly, depending upon the detailed method of synthesis and specific plant extract used.

*Aspergillus fumigatus* is a common pathogenic fungus that is the main cause of invasive pulmonary aspergillosis (IPA). IPA is associated with a high risk of unsuccessful treatment and mortality due resistance to almost known antifungal drugs including Amphotericin B. and Triazole.

Thus, nanoparticles synthesized using an environmentally friendly method solving the aforementioned problems are desired.

SUMMARY

The present subject matter relates to an eco-friendly method for preparing a silver nanoparticle composition. The silver nanoparticle composition or *Salsola tetrandra* silver nanoparticles (ST-AgNPs) can be prepared by providing a *Salsola tetrandra* extract and combining the *Salsola tetrandra* extract with silver nitrate. In an embodiment, the mixture can be heated to complete the bio-reduction process and provide the *Salsola tetrandra* silver nanoparticle composition. In an embodiment, the *Salsola tetrandra* silver nanoparticles can be used to treat or inhibit a fungal infection. In an embodiment, the fungal infection can be administered to a subject to treat invasive pulmonary aspergillosis.

In an embodiment, the present subject matter relates to a method of synthesizing *Salsola tetrandra* silver nanoparticles, comprising: mixing a *Salsola tetrandra* extract with a silver nitrate solution to provide a mixture, heating the mixture to obtain a heated solution including *Salsola tetrandra* silver nanoparticles, and isolating the *Salsola tetrandra* silver nanoparticles from the heated solution.

According to an embodiment, the present subject matter relates to silver nanoparticles prepared by the methods as described herein.

According to an embodiment, the present subject matter relates to a pharmaceutical composition comprising the *Salsola tetrandra* silver nanoparticles and a pharmaceutically acceptable carrier. In an embodiment, a method of treating invasive pulmonary aspergillosis comprises administering a therapeutically effective amount of the pharmaceutical composition to a subject in need thereof.

These and other features of the present subject matter will become readily apparent upon further review of the following specification and drawings.

DETAILED DESCRIPTION OF THE PREFERRED EMBODIMENTS

Figure 1:
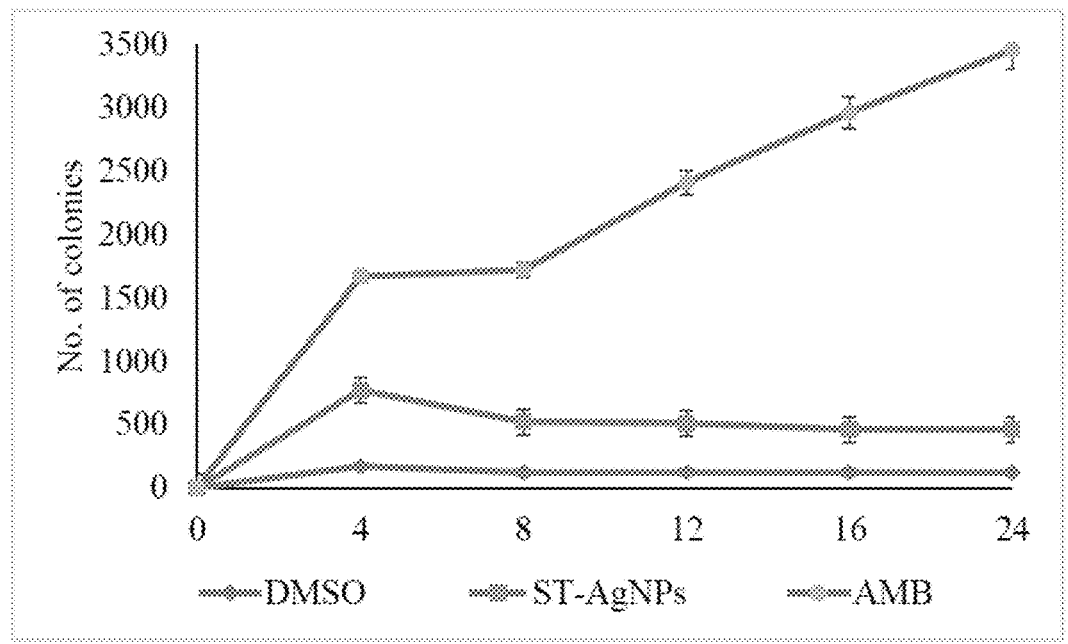
FIG. 1 is a graph showing time-kill curves of *A. fumigatus* following exposure to ST-AgNPs and amphotericin B for 24 hours (values are expressed as means±SD)

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

A "subject" herein is typically a human. In certain embodiments, a subject is a non-human mammal. Exemplary non-human mammals include laboratory, domestic, pet, sport, and stock animals, e.g., mice, cats, dogs, horses, and cows. As used herein, the term "patient" refers to any single subject for which treatment is desired. In certain embodiments, the patient herein is a human. A subject can be considered to be in need of treatment.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

The present subject matter relates to *Salsola tetrandra* silver nanoparticles (ST-AgNPs) (also referred to herein, as *Salsola tetrandra* silver nanoparticle composition or nanocomposite). The *Salsola tetrandra* silver nanoparticles may be synthesized by providing a *Salsola tetrandra* extract and combining the *Salsola tetrandra* extract with silver nitrate. In an embodiment, the mixture can be heated to complete the bio-reduction process and provide the *Salsola tetrandra* silver nanoparticle composition.

In an embodiment, the extract may be synthesized by harvesting *Salsola tetrandra* leaves, drying the *Salsola tetrandra* leaves, powdering the dried *Salsola tetrandra* leaves, mixing the powdered *Salsola tetrandra* leaves with a solvent to provide a solution, and extracting the solution to provide a plant extract. In an embodiment, the solvent can be an alcohol, e.g., ethanol. The silver nitrate, e.g., an aqueous solution of silver nitrate, can be added to the plant extract to provide a mixture including the *Salsola tetrandra* silver nanoparticles.

In an embodiment, about 100 mL solution of silver nitrate ($AgNO_3$) (about 10 mM) can be added to about a 200 mL solution of the plant extract (about 500 µg/mL) to provide the mixture. In an embodiment the solution of silver nitrate can be an aqueous solution. The silver nitrate can reduce the plant extract into Ag+ ions. For example, the mixture can be heated at a temperature of about 80° C. for about 3 hours with stirring. A color change in the mixture from colorless to pale brown can indicate synthesis of the *Salsola tetrandra* nanoparticle composition (ST-AgNPs).

In an embodiment, the ST-AgNPs can be separated by centrifugation. In an embodiment, the pellet can be re-dispersed in water, centrifuged, and lyophilized to provide a ST-AgNPs powder. In an embodiment, the ST-AgNPs can be separated by centrifugation at about 15,000 g for about 30 minutes. UV-visible spectrophotometry can be used to verify the formation of ST-AgNPs, that presented surface plasmon resonance (SPR) at 420 nm.

An embodiment of the present subject matter is directed to a pharmaceutical composition comprising the *Salsola tetrandra* silver nanoparticle composition and a pharmaceutically acceptable carrier.

An embodiment of the present subject matter is directed to a method of making a pharmaceutical composition including mixing the *Salsola tetrandra* silver nanoparticle composition with a pharmaceutically acceptable carrier. For example, the method of making a pharmaceutical composition can include mixing the *Salsola tetrandra* silver nanoparticle composition under sterile conditions with a pharmaceutically acceptable carrier with preservatives, buffers, and/or propellants to create the pharmaceutical composition.

To prepare the pharmaceutical composition, the *Salsola tetrandra* silver nanoparticle composition, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The *Salsola tetrandra* silver nanoparticle composition be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the *Salsola tetrandra* silver nanoparticle composition or an amount effective to treat a disease, such as a fungal infection, may be determined initially from the Examples described herein and adjusted for specific targeted diseases using routine methods.

The *Salsola tetrandra* silver nanoparticle composition can have antifungal properties. In an embodiment, the *Salsola tetrandra* silver nanoparticle composition can be administered to a subject in need thereof to inhibit fungal growth. In an embodiment, the *Salsola tetrandra* silver nanoparticle composition can inhibit the growth of *Aspergillus fumigatus*. In an embodiment, the *Salsola tetrandra* silver nanoparticle composition can be administered to a subject in need treat a fungal infection, such as invasive pulmonary aspergillosis.

In a further embodiment, the *Salsola tetrandra* silver nanoparticle composition can be administered to a subject in need thereof to treat invasive pulmonary aspergillosis. In an embodiment, the *Salsola tetrandra* silver nanoparticle composition can be formulated as an aerosol for administration to a patient in need thereof.

According to an embodiment, an aerosol formulation of the *Salsola tetrandra* silver nanoparticle composition can include about 0.1% w/v to about 0.3% w/v of an aqueous solution of the ST-AgNPs and about 2% to about 5% propellant. In an embodiment, the aerosol formulation of the *Salsola tetrandra* silver nanoparticle composition can include about 0.1% w/v of the aqueous solution of ST-AgNPs (about 10 mg/mL) and about 2% propellant. In an embodiment, a metered-dose aerosol formulation can provide about 100 micrograms of the aerosol formulation per dose.

An embodiment of the present subject matter is directed to a method of inhibiting fungal growth in a subject, comprising administering to a subject in need thereof a therapeutically effective amount of the pharmaceutical composition according to the present subject matter. In an embodiment, the present subject matter is directed to a method of treating a fungal infection in a subject, comprising administering to a subject in need thereof a therapeutically effective amount of the pharmaceutical composition according to the present subject matter. In an embodiment, the fungal infection is invasive pulmonary aspergillosis.

The *Salsola tetrandra* silver nanoparticle composition or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

Example 1

Silver Nanoparticle Synthesis Using *Salsola tetrandra*

A 200 mL solution of alcoholic leaf extract of *Salsola tetrandra* (500 µg/mL) was mixed with 100 mL solution of silver nitrate ($AgNO_3$) (10 mM). The two solutions were mixed together and heated at 80° C. for 3 hours with stirring. The complete reduction was verified by a change in color from colorless to pale brown. The *Salsola tetrandra* silver nanoparticles ST-AgNPs were separated by centrifugation at 15,000 g for 30 min. The pellet was re-dispersed in water, centrifuged, and lyophilized to obtain ST-AgNPs powder. UV-visible spectrophotometry was used to verify the formation of ST-AgNPs, that presented surface plasmon resonance (SPR) at 420 nm. The green, biosynthesized composite AgNPs using *Salsola tetrandra* were characterized by imaging (transmission electron microscopy (TEM), UV-VIS spectroscopy, zeta potential, X-ray diffraction (XRD), Energy dispersive x-ray analysis (EDX), and Fourier transform infrared spectroscopy (FTIR).

Example 2

Activity Against *Aspergillus fumigatus*

Figures 2A, 2B, 2C:
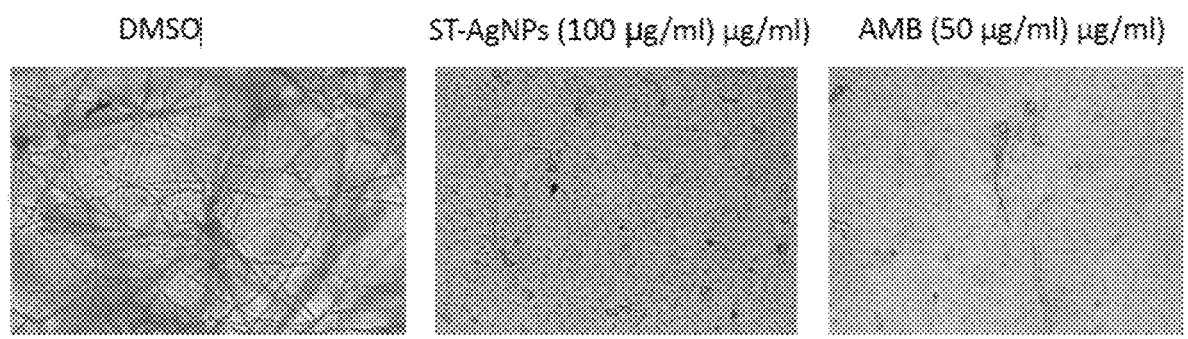
FIGS. 2A-2C show differences in the mycelial growth of *A. fumigatus* in 2A) control 2B) following exposure to ST-AgNPs and 2C) following exposure to amphotericin B. (conventional antifungal agent).

Several preliminary in vitro experiments were performed to confirm the potent antifungal potential of the green biosynthesized silver nanoparticles (ST-AgNPs) against *A. fumigatus*. The results of a time kill assay revealed the fungistatic action of the positive control (DMSO), amphotericin B (AMB) and ST-AgNPs at 50 µg/mL and 100 µg/mL, respectively, on the growth of *Aspergillus* cells (FIG. 1). Additionally, the inhibitory effect of the antifungals AMB and ST-AgNPs was also examined using light microscopy (FIGS. 2A-2C). Mycelial growth substantially reduced using AMB (FIG. 2C). Interestingly, treatment of *A. fumigatus* with ST-AgNPs significantly reduced the germination rate of the fungus (FIG. 2B).

It is to be understood that the silver nanoparticles are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing *Salsola tetrandra* silver nanoparticles, comprising:
   mixing a *Salsola tetrandra* ethanol extract with a silver nitrate solution to provide a mixture; and
   heating the mixture to obtain a heated solution including *Salsola tetrandra* silver nanoparticles.

2. The method of claim 1, further comprising isolating the *Salsola tetrandra* silver nanoparticles from the heated solution by:
   centrifuging the heated solution including the *Salsola tetrandra* silver nanoparticles to separate the *Salsola tetrandra* silver nanoparticles from the heated solution;
   redispersing the *Salsola tetrandra* silver nanoparticles in water to obtain a *Salsola tetrandra* silver nanoparticle dispersion; and
   centrifuging the *Salsola tetrandra* silver nanoparticle dispersion to obtain isolated *Salsola tetrandra* silver nanoparticles.

3. The method of claim 1, wherein the *Salsola tetrandra* ethanol extract is a *Salsola tetrandra* leaf extract.

4. The method of claim 3, wherein about 100 mL solution of silver nitrate ($AgNO_3$) is added to about a 200 mL solution of the *Salsola tetrandra* ethanol extract to provide the mixture.

5. The method of claim 1, wherein the mixture is heated at a temperature of about 80° C. for about 3 hours.

6. The method of claim 2, further comprising lyophilizing the isolated *Salsola tetrandra* silver nanoparticles after centrifuging to obtain lyophilized *Salsola tetrandra* silver nanoparticles (ST-AgNPs) powder.

7. *Salsola tetrandra* silver nanoparticles prepared by the method of claim 1.

8. A pharmaceutical composition, comprising the *Salsola tetrandra* silver nanoparticles of claim 7 and a pharmaceutically acceptable carrier.

9. A method of inhibiting fungal growth in a subject, comprising administering a therapeutically effective amount of the pharmaceutical composition of claim 8 to a patient in need thereof.

10. The pharmaceutical composition of claim 8, further comprising a propellant.

11. A method of treating a fungal infection in a patient, comprising administering a therapeutically effective amount of the pharmaceutical composition of claim 10 to a patient in need thereof.

12. The method of claim 11, wherein the fungal infection is invasive pulmonary aspergillosis.

13. A method of synthesizing *Salsola tetrandra* silver nanoparticles, comprising:
   mixing a *Salsola tetrandra* ethanol extract with a silver nitrate solution to provide a mixture;
   heating the mixture to obtain a heated solution including *Salsola tetrandra* silver nanoparticles; and
   isolating the *Salsola tetrandra* silver nanoparticles from the heated solution.

14. The method of claim 13, wherein isolating the *Salsola tetrandra* silver nanoparticles from the heated solution comprises:
   centrifuging the heated solution including the *Salsola tetrandra* silver nanoparticles to separate the *Salsola tetrandra* silver nanoparticles from the heated solution;
   redispersing the *Salsola tetrandra* silver nanoparticles in water to obtain a *Salsola tetrandra* silver nanoparticle dispersion; and
   centrifuging the *Salsola tetrandra* silver nanoparticle dispersion to obtain isolated *Salsola tetrandra* silver nanoparticles.

15. The method of claim 14, wherein the mixture is heated at a temperature of about 80° C. for about 3 hours.

16. The method of claim 15, further comprising lyophilizing the isolated *Salsola tetrandra* silver nanoparticles after centrifuging to obtain lyophilized *Salsola tetrandra* silver nanoparticles (ST-AgNPs) powder.

* * * * *